United States Patent [19]

Ishii et al.

[11] 4,017,733

[45] Apr. 12, 1977

[54] IONIZATION TYPE SMOKE SENSOR

[75] Inventors: Kanji Ishii; Haruyoshi Sato, both of Tokyo, Japan

[73] Assignee: Hochiki Corporation, Tokyo, Japan

[22] Filed: Apr. 17, 1975

[21] Appl. No.: 568,969

[30] Foreign Application Priority Data

Apr. 18, 1974 Japan .................. 49-44089[U]
Dec. 12, 1974 Japan .................. 49-141990

[52] U.S. Cl. .......................... 250/381; 250/385
[51] Int. Cl.² .................. G01T 1/18; H01J 39/28
[58] Field of Search ........ 250/381, 382, 384, 385, 250/389

[56] References Cited

UNITED STATES PATENTS 3,448,261  6/1969  Amiragoff ................ 250/381
3,767,917  10/1973  Lampart et al. ............ 250/385 X Primary Examiner—Archie R. Borchelt
Attorney, Agent, or Firm—Frank J. Jordan

[57] ABSTRACT

In a smoke sensor of the ionization type having as essential component parts an opposing pair of electrodes providing for high impedance effected by ionic current produced by a radioactive ray source, improvements are made to eliminate formation of dew at least on the surface of the radioactive ray source and also prevent the high impedance from being accidentally changed due to a cause other than smoke, for instance a comparatively intense air stream which may otherwise cause a casual change of the high impedance.

7 Claims, 26 Drawing Figures

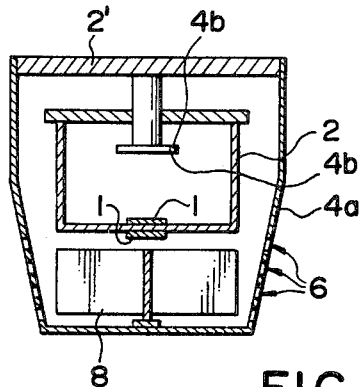
FIG. 4a Prior Art
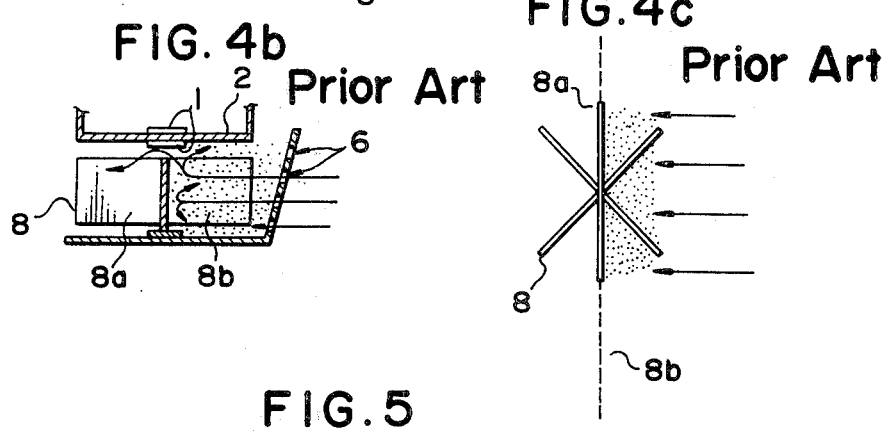
FIG. 4b Prior Art
FIG. 4c Prior Art
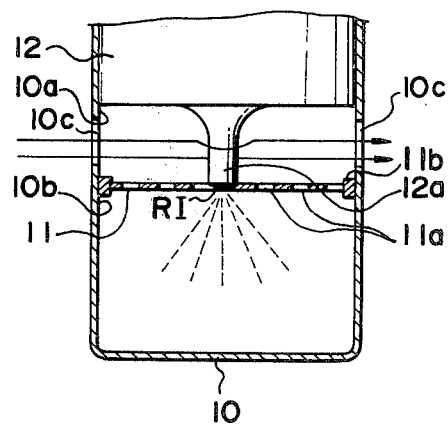
FIG. 5

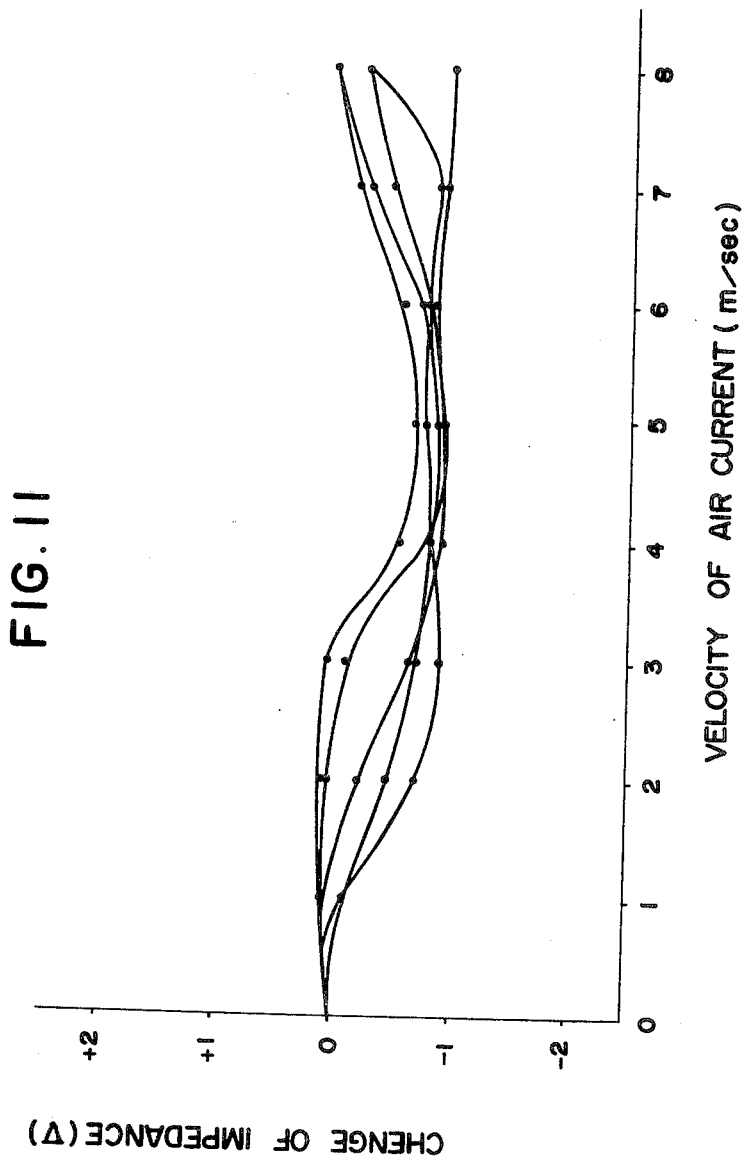

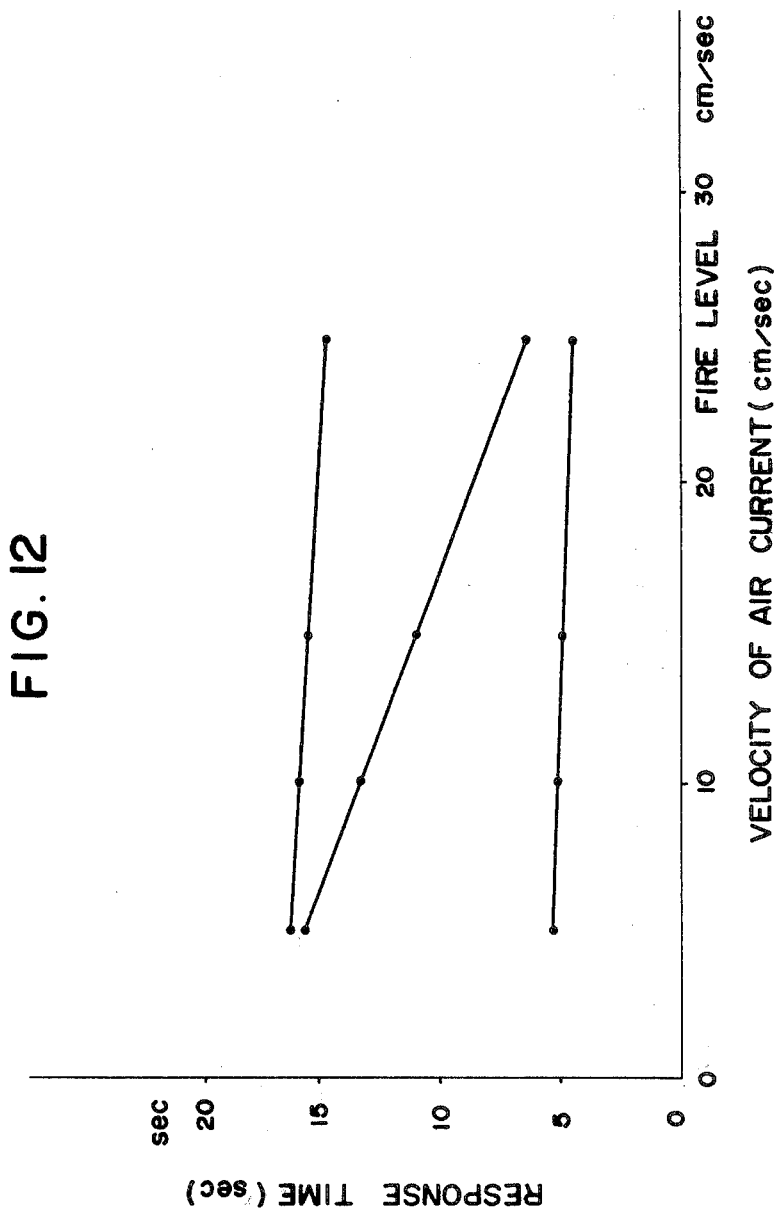

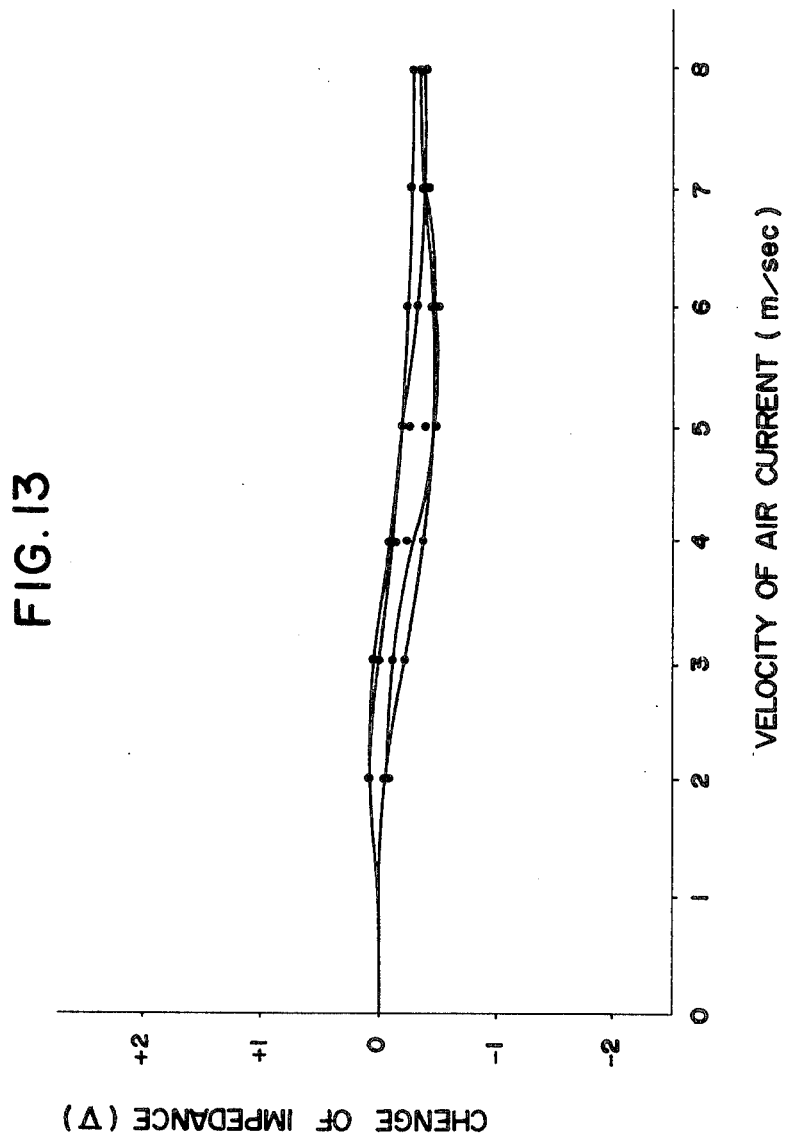

IONIZATION TYPE SMOKE SENSOR

DETAILED DESCRIPTION OF THE INVENTION

This invention relates to smoke sensors of the ionization type for sensing smoke with high sensitivity in terms of a change of high impedance of an opposing pair of electrodes due to a corresponding change in ionic current produced from a source of radioactive rays, and it aims to solve the problem of malfunction of falsely sensing smoke due to a casual change of the impedance resulting from a cause other than smoke, particularly due to formation of dew in the sensor or introduction of a comparatively intense air stream into the sensor.

The preclusion of the false detection of smoke due to the disturbance of the ionic current flux caused by a comparatively intense air stream entering the sensor, which constitutes one of the objects of the invention, is accomplished with, for instance, a smoke sensor disclosed in U.S. Pat. No. 3,731,093. This sensor utilizes a cup-like, double-wall structure consisting of inner and outer sheathing walls formed with respective windows at respectively different positions to provide for an appropriate resistance to the flow of an incoming air stream. With this arrangement, the speed of the air stream is reduced in a non-linear fashion to permit the reduction or weakening of the effects of the air stream upon ionic current flux. However, such a simple construction cannot permit the control of formation of dew within the sensor even with a slight sacrifice in response compared to smoke sensors without any means to provide resistance to the flow.

While the formation of dew on the surface of the source of radioactive rays, causing a change of the ionic current flux, has already been recognized as a significant problem left unsolved, it should be thought also to ultimately constitute a cause of the malfunction that will occur as a result of introduction of a casual air stream. This is because the dew that is formed is attributable to moisture carried by the air stream.

In the light of the above, the invention provides improvements over the prior-art ionization type smoke sensors, which are readily prone to malfunction because of the requirement for high sensitivity, on the principles of an incoming air stream flow control method which permits simultaneous achievement of the aforementioned two objects.

BRIEF DESCRIPTION OF THE DRAWINGS

FIG. 4a is a sectional view of a construction disclosed in the Japanese Utility Model Application Publication No. 42549/1973;

FIG.

FIG. 4b is a view showing a lower portion of the construction of FIG. 4a with a showing of the behavior of the same with respect to an incoming air stream;

FIG. 4c shows in plan view an ionic current flux distributing structure in the same lower part of the construction.

Figure 6A:
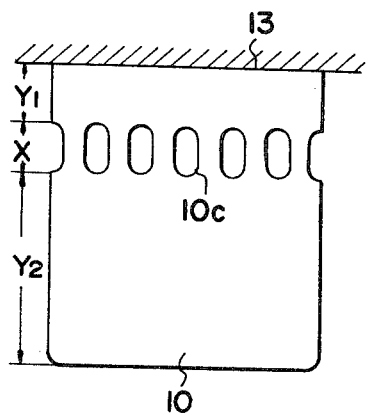
Figure 6B:
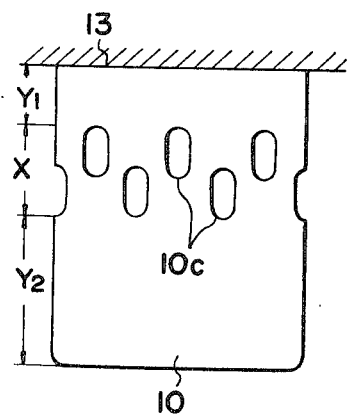
Figure 7:
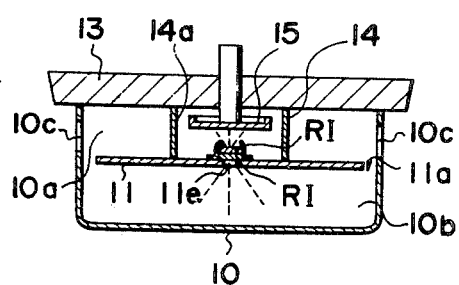
Figure 8A:
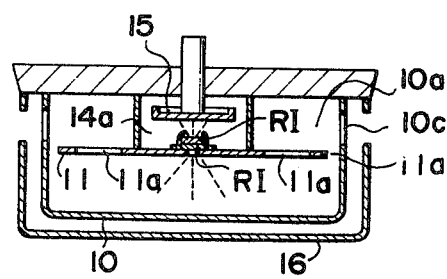
Figure 8B:
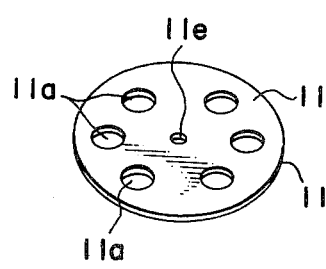
Figure 8C:
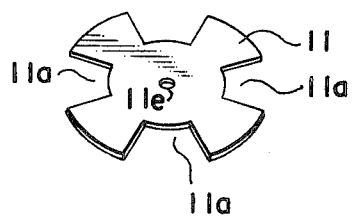
Figure 9A:
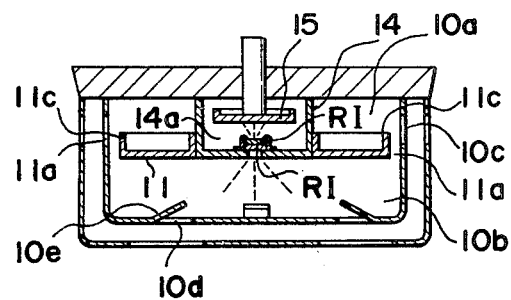
Figure 9B:
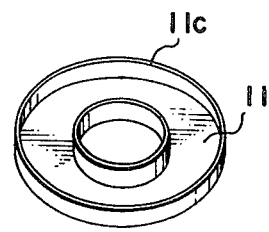

FIG. 5 is a sectional view showing a model of the construction of the smoke sensor embodying the invention;

FIG. 6a is an elevational view showing an example of the cup-shaped outer electrode used for the ionization type smoke sensor according to the invention;

FIG. 6b is a view similar to FIG. 6a but showing a different example of the cup-shaped outer electrode having a different arrangement of windows;

FIG. 7 is a sectional view showing another embodiment of the smoke sensor according to the invention;

FIG. 8a is a sectional view showing still another embodiment of the smoke sensor;

FIG. 8b is a perspective view showing an example of the intermediate electrode to be used in the smoke sensor according to the invention;

FIG. 8C is a perspective view showing a different example of the intermediate electrode;

FIG. 9a is a sectional view showing a further embodiment of the smoke sensor;

FIG. 9b is a perspective view showing an intermediate electrode used in the embodiment of FIG. 9a;

FIGS. 10a to 10e are perspective views showing respective examples of the second electrode to be used for the construction of the invention type smoke sensor according to the invention;

FIG. 11 is a graph showing the effects of comparatively intense air streams entering a prior-art ionization type smoke sensor upon the ionic current flux produced therein.

Figure 14A:
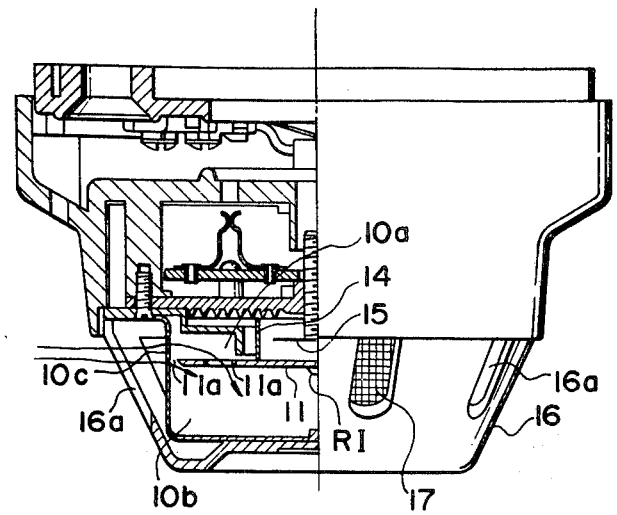
Figure 14B:
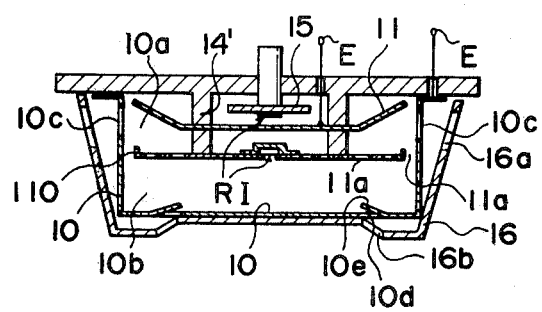
Figure 14C:
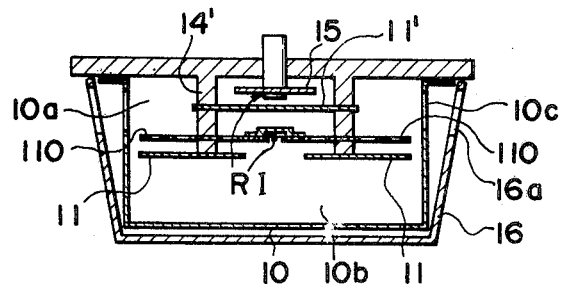

FIG. 12 is a graph showing the detection sensitivity or response characteristic of some smoke sensors having means to provide resistance to the flow of incoming air streams and a one without any such means;

FIG. 13 is a graph showing the effects of comparatively intense air streams entering an ionization type smoke sensor according to the invention upon the ionic current flux;

FIG. 14a is an elevational view, partly in section, showing a still further embodiment of the ionization type smoke sensor according to the invention; and FIGS. 14b and 14c are sectional views showing modifications of the embodiment of FIG. 14a.

It is to be understood that the various embodiments of the invention illustrated in the drawings are by no means limitative, and further various changes and modifications in the design for obtaining the function of controlling the flow of incoming air streams may be wider according to details hereinafter covered by the invention.

For a fuller understanding of the invention, some examples of the prior-art construction of a ionization type smoke detector will first be described in connection with FIGS. 1 to 3 and 4a to 4c.

Figure 1:
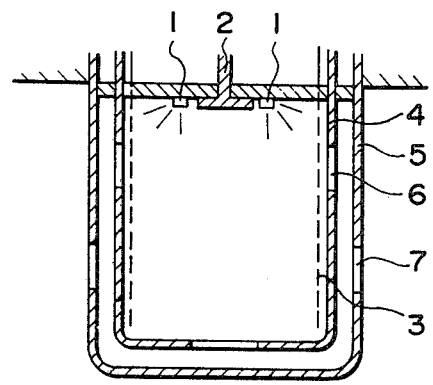
FIG. 1 is a sectional view showing the inner construction of the afore-mentioned smoke sensor disclosed in U.S. Pat. No. 3,731,093.
Figure 2:
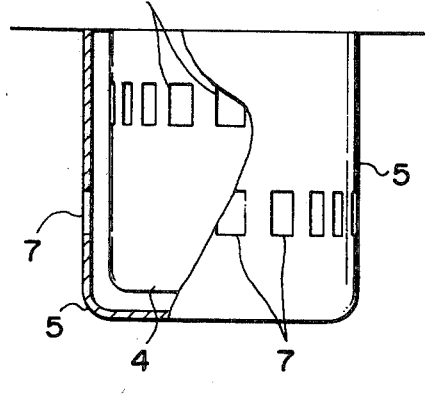
FIG. 2 is a partly brokenaway elevational view of the same smoke sensor.

In the example of FIGS. 1 and 2, a pair of radioactive ray sources 1 are disposed on opposite sides of an inner electrode 2, and an opposing outer electrode 3 is enclosed by a protective cup-shaped double-wall structure consisting of inner and outer sheathing walls 4 and 5, which are formed with respective windows 6 and 7, the windows 6 being located at positions different with respect to the windows 7. With this arrangement of windows, air streams entering the sensor makes a turn around the inner sheathing wall before entering the interior thereof. In this way, adequate resistance to the flow of the incoming air streams is provided to reduce the speed thereof so as to prevent excessive disturbance of the ionic current flux. However, moisture carried along by the air stream cannot be removed by such flow resistance affording means, so it results in the formation of much dew in the interior of the cup 4. The formation of dew is most likely to result on the surfaces of metal parts such as electrodes which are at the lowest temperature among the parts constituting the construction of the sensor; if the radioactive ray sources 1 are sealed within metal parts, the surfaces thereof are also likely to be wetted with dew. If the incoming air stream has a relative humidity of 50 to 60 percent, attachment of dew to the metal parts will readily result when the temperature of the metal parts is lower than that of the air stream by about 20° C.

Also, if the relative humidity of the air stream is 70 to 80 percent, a temperature difference of about 10° C. will give rise to the attachment of dew.

Such conditions for the attachment of dew are very frequently met in the above smoke sensors; as soon as such a condition is met, the interior of the sensor is subject to the formation of dew, even though it may be little in amount. By way of example, in the interior of an artificially air-conditioned building, where the heat mass of the building as a whole is predominantly greater than that of the space available for use, the afore-mentioned condition of temperature difference of 10° to 20° C. between the air stream in the space in use and the component metal parts of the smoke sensor will always be met at the time of starting or stopping the air conditioning system. At the time of heating the room, the temperature of the room space rises prior to that of the building. Consequently, the condition for the formation of dew is satisfied when heating the room from 0° C. to a suitable room temperature of around 20° C. In the case of cooling the room, the temperature of air streams in the space in use is elevated prior to that of the building at the time of stopping the air conditioning system, thus providing for the condition for the formation of dew.

Figure 3:
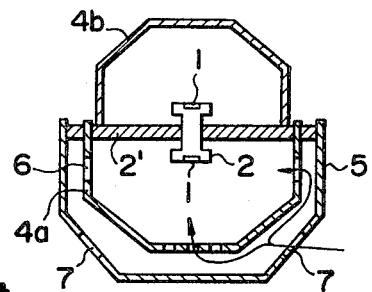
FIG. 3 is a sectional view of a construction disclosed in the Japanese Utility Model Application Publication No. 9058/1971.

FIG. 3 shows a different prior-art example, in which a cup-shaped outer electrode 4a is accomodated within a sheating member 5, these parts constituting a double-wall structure and being formed with respective windows 6 and 7 located at different positions relative to one another. Also, a cup-shaped inner electrode 4b is provided on the side of an insulating base 2' opposite the outer electrode 4a, and an intermediate electrode 2 secured to and penetrating the base 2' has its opposite ends face the respective inner and outer electrodes 4a and 4b and form two electrode pairs, with radioactive ray sources 1 being each carried at each end of it.

FIGS. 4a to 4c show a further prior-art example. Here, a cup-shaped intermediate electrode 2 is disposed within an outer electrode 4a, and an inner electrode 4b extends into the intermediate electrode 2. Radioactive ray sources 1 are mounted on each side of the bottom portion of the cup-shaped intermediate electrode 2 facing the inner electrode 4b and the outer electrode 4a respectively. The ionic current flux produced by the radioactive ray source 1 facing the outer electrode 4a is distributed by an intervening distributing structure 8 consisting of a plurality of radially arranged plate members (as is most clearly shown in FIG. 4c). The outer electrode 4a is formed in its lower portion adjacent to its bottom with windows 6 which face the distributing structure 8. With this construction, an air stream coming, for instance, from the right hand in the Figure is trapped in a zone 8b to disturb part of the ionic current flux that is distributed in this zone while it stays there without substantially affecting the rest of the ionic current flux distributed in the remaining zone 8a.

This arrangement, though it may preclude or reduce the possibility of malfunction that might result from the intrusion of a casual air stream, has a disadvantage in that only a division of the total ionic current flux is effectively utilized for the detection of smoke. Therefore, the regular sensitivity of detection will be reduced, or it will be necessary to increase the intensity of the radioactive radiation that is used. Since this arrangement for dividing the space available for detection leads to substantial reduction of the sensitivity, the previously mentioned flow resistance producing means which is capable of affording exponentially increasing resistance with increase in the air stream intensity is principally preferred to the space dividing means insofar as the prevention of malfunction stemming from the intrusion of a comparatively intense casual air stream is concerned.

FIG. 5 shows a basic model of the ionization type smoke sensor according to the invention, and this model may be appropriately modified to obtain the practical effects that are attainable according to the invention as will be discussed hereinafter.

The principles underlying the invention reside in utilizing a construction, which permits to effectively make use of the heat possessed by an incoming air stream that may otherwise give rise to the formation of dew for reducing the temperature difference between the air stream and the main component part such as electrode or radioactive ray source to an extent effective in breaking down the condition required for the formation of dew. In fact, no dew is formed on the main component part if its temperature is higher than that of the air stream. In practice, effective reduction of temperature difference to an extent effective in preventing the dew forming condition from being set up can be obtained by so arranging as to let the heat of the air stream be transferred to the main component part of the sensor, thereby reducing the temperature of the air stream while at the same time increasing the temperature of the main component part as much as possible.

Referring now to FIG. 5, reference numeral 10 designates a first electrode member having a cup-like form and constituting one of the pair electrodes (preferably outer electrode). The interior of the cup-shaped first electrode member 10 is divided into upper and lower sections 10a and 10b by a second electrode member 11 transversely extending within the first electrode member.

The first electrode member 10 is formed in its peripheral wall portion defining the upper section 10a with circumferentially arranged openings or windows 10c. The second electrode member 11 is formed with inlet openings or holes 11a. The top opening of the first electrode member 10 is closed by a base member 12 having a pole 12a extending toward the second electrode member 11. By virtue of this pole 12a an air stream entering the upper section 10a through some of the openings 10c is caused to whirl there. In other words, the pole 12a causes the air stream entering the upper section 10a to be trapped in and stay there for an extended period of time. In consequence, the second electrode member 11 which is made of a metal can receive heat from the air stream to elevate its temperature to an extend close to the resulting temperature of the air stream.

At the same time, the resultant air streams flowing in disorderly directions caused by the pole 12a, enter, while reducing the flow speed, through the inlet openings 11a into the lower section 10b. A radioactive ray source RI consisting of, for instance, $Am^{241}$ or other isotopes is carried by the pole 12a at the tip thereof or by the transversal second electrode member 11 at a position corresponding to the pole tip, and it provides an ionic current flux distributed in the lower section 10b. With this construction, the ionic current flux will not be disturbed by the reduced-speed air streams entering through the inlet openings 11a to such an extent as to cause a malfunction of falsely detecting smoke; at least the loss of ions flowing to the outside of the lower section can be eliminated.

FIGS. 6a and 6b show examples of the cup-shaped first electrode member 10, which may be formed by press working a thin metal plate. The openings 10c are oval in the illustrated examples and are arranged in a row in the example of FIGS. 6a and in a staggered fashion in the example of FIGS. 6b, they may have various forms and be arranged in a variety of other arrangements as well. The area X for the arrangement of openings 10c is made large enough to permit sufficient air flow for ensuring sufficiently high sensitivity. Labeled $Y_1$ and $Y_2$ are regions over which the interior of the first electrode member is sheathed from the outside. Designated at 13 is a ceiling, and at 11b is an insulator for electrically insulating the first and second electrode members 10 and 11 from each other.

This basic model features that heat is effectively taken from the air stream while it whirls in disordely directions within the upper section 10a in direct contact with the first and second electrode members 10 and 11, which are metal parts, so that it is possible to provide an excellent heat extraction efficiency which cannot be expected from a prior-art construction having flow resistance affording means provided on the outer side of an outer electrode corresponding to the first electrode member. With this construction, dew is formed on the wall surfaces defining the upper section 10a, and the resultant air stream reduced in its relative humidity to the corresponding extent flows into the lower section 10b. Also, the walls constituting the lower section 10b, particularly the radioactive ray source RI held in contact with the second electrode member, have been brought, due to the conduction of the transferred heat, to be in an elevated temperature condition close to the reduced temperature of the resultant air stream enters the lower section, whereby the formation of dew can be reduced to an extent sufficient to preclude the setting-up of a condition necessary to the formation of dew. While the attachment of dew to the wall surfaces of the lower section 10b is effectively avoided in the above manner, the wall surfaces of the upper section 10a in which dew is preferentially formed belong to a region irrelevant to the detection of smoke, that is, dew formed in the upper section does not have any adverse effect upon the function of smoke detection at all. The instant model of the smoke sensor resistance is connected in series with either a high resistance element or another closed ionization chamber having a comparative high-impedance as in the usual practice, and it is arranged such that upon a change of the impedance of the lower section caused by intrusion of smoke carried by air stream entering there a division of voltage applied therefore is changed to produce a response output. As a practical example, an applied voltage of 17 volts and a division voltage of 7 volts may be preset.

Figure 10A:
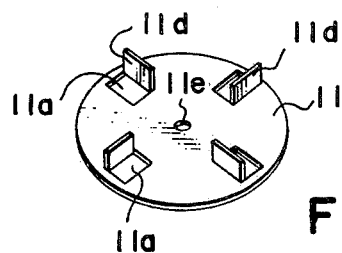
Figure 10B:
Figure 10C:
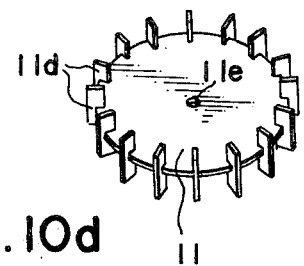
Figure 10D:
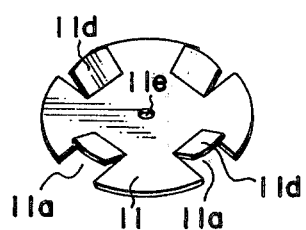
Figure 10E:
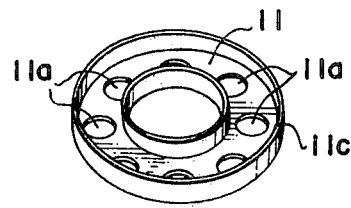

FIGS. 7, 8a and 9a show embodiments where the aforementioned closed ionizing chamber is formed within the first electrode member of a cup-shaped form to achieve the objects of the invention. The closed ionizing chamber is defined by a third electrode member 14, which is coupled to second electrode member 11 (preferably serving as intermediate electrode here) such that it is disposed within upper section 10a, and an inner electrode 15 is disposed within this closed ionizing chamber. Since the third electrode member 14 is made of metal, it has a high heat receiving efficiency and is also able to cause formation of much dew, thus aiding in the prevention of dew formation in lower section 10b. In the embodiment of FIG. 7, a gap 11a formed between the first and second electrode members 10 and 11 has the role of opening means. The opening means may be formed in the second electrode member 11 in various forms and arrangements as shown in FIGS. 8a, 8b, 9b and 10a to 10e. The member of FIG. 8b is formed with radially spaced circular openings 11a. The member of FIG. 8c has peripheral notches 11a which constitute a basic form of opening means. Further, for the purpose of causing the whirling of the air stream in the upper section 10a it is effective to provide the second electrode member with a peripheral annular projection 11c extending into the upper section, as shown in FIGS. 9b and 10e. In the examples of FIGS. 10a to 10d, fins 11d are provided adjacent to respectively associated opening means. Where fins are formed at right angles to the plane of opening means (as in FIGS. 10a and 10c examples), external air streams are led to the upper section 10a. In the example of FIG. 10d, the fins 11d are formed at an angle with respect to the respectively associated opening means 11a, and they can permit part of air stream entering the upper section 10a to be led to the lower section 10b. Thus, where high sensitivity is required for the smoke sensor, they can serve as effective means to meet this requirement. In the example of FIG. 10b, the fins 11b formed adjacent to the respective openings 11a act to substantially close opening 10c nearest to them, while having no substantial closing effect with respect to remote openings 10c located on the side of the center of the member opposite them. This means that an air stream entering through some openings 10c into the upper section 10a will stay here for a while before it is led to the lower section 10b.

The instant embodiments of FIGS. 7, 8a and 9a each incorporate means to mount a radioactive ray source RI within the cup-shaped third electrode member 14 which is sealed against intrusion of external air streams. More particularly, a central portion of the second electrode member 11 is formed with radially spaced holes for mounting the radioactive ray source RI on the second electrode member on the side of the third electrode member 14.

Where the peripheral annular projection 11c is provided on the second electrode member 11, it may partly overlap the openings 11c formed in the first electrode member 10. Likewise, the position of the periphery of the second electrode member 11 without any peripheral annular projection relative to the openings may be appropriately selected. This is so because the basic construction according to the invention, which permits reduction in the difference of the temperature of the incoming air stream with respect to a lower temperature of the main metal component parts of the senosr to an extent no longer sufficient to the formation of dew, has an important feature that the air stream is affected to stay in the upper section where dew is to be formed preferentially for a comparatively long time, during which period the metal parts can take heat from the air stream. The metal parts, the temperature difference of which with respect to the air stream has thus been reduced, will be under a condition hardly prone to dew formation from the thermal standpoint. Under this condition, even if part of an air stream entering the sensor directly flows into the lower section 10b where the ionic current flux is distributed, the dew formation there can be well precluded for the direct air stream is mixed with air having been deprived of moisture as dew formed in the upper section and reduced in the relative humidity. The proportion of air directly permitted to the lower section 10b may be altered depending upon the degree of relative humidity that is roughly expected from the climate and weather of countries.

FIG. 11 shows changes of the impedance between a pair of electrodes of a prior-art smoke sensor construction having an open ionization chamber (corresponding to the lower section 10b mentioned above) formed with windows where air streams entering therethrough directly affect the ionic current flux, the changes being caused due to corresponding disturbances of the ionic current flux, while FIG. 13 is a typical showing of impedance changes due to corresponding effects of air streams upon a smoke sensor according to the invention. In these Figures, the impedance is shown in terms of a division of a voltage between the pair of electrodes, with design voltage set to 0 volt. In the case of the prior-art open ionization chamber without any protective means with respect to direct air streams, the ionic current flux is subject to considerable disturbances with air speeds exceeding about 3 m/sec. (as is seen from FIG. 11). In contrast, with the smoke sensor according to the invention the disturbance of the ionic current flux can be effectively suppressed to effectively preclude casual changes of the division voltage, as is seen from FIG. 13. The group of curves in each of these FIGURES indicates that the impedance change is various depending upon each of the incoming air streams even with the same speed.

FIG. 12 compares the response characteristic of the smoke sensor according to the invention, which permits to reduce the speed and relative humidity of incoming air streams and effect heat transfer therefrom to the main metal component parts. With a knowledge that most air streams produced at the time if fire accidents have a speed of about 25 cm/sec., the response time of various smoke sensors from the reaching of smoke carrying air streams to the inlet windows of the sensor till the delivery of a detection alarm has been tested, the smoke carrying air streams being produced in a firewise manner and caused to reach the sensor at various speeds.

The afore-mentioned prior-art smoke sensor having an open ionization chamber corresponding to the lower section 10b and provided with inlet windows permitting incoming air streams to flow directly into the space between the pair electrodes took a substantially equal response time, 5 seconds in the experiments, with respect to air streams with speeds ranging from 5 cm/sec. to 25 cm/sec. as shown by curve $\delta$. This means that this smoke sensor has high sensitivity even with respect to gentle air streams.

In the case of the smoke sensor according to U.S. Pat. No. 3,731,093 mentioned earlier, having a cup-shaped double-wall structure affording resistance to comparatively intense air streams, the detection is slower with respect to the afore-mentioned gentle air streams of 5 cm/sec. to 25 cm/sec., as shown by curve $\beta$.

The response characteristic of the smoke sensor according to the invention is shown by curve 60. As is seen from this curve, although the detection is comparatively slow like the case of the above smoke sensor with resistance providing means with respect to very gentle air streams with speeds less than 20 cm/sec., it is possible to provide the substantially same response time as with the sensor without any flow resistance affording means with respect to air streams flowing at speeds exceeding 25 cm/sec. corresponding to the speed of air streams occurring at the time of fire accidents.

It is to be noted that these plots were obtained in investigating the relation between response time and flow speed in tests where the concentration of smoke carried by the air stream was held very low (about 15 percent), and the response will be faster with all the above sensors with respect air streams where the concentration of smoke or combusted matter corresponds to what results at the time of occurence of a fire.

FIG. 14a shows a further embodiment, in which second and third electrode members 11 and 14 are joined to each other and accommodated altogether in cup-shaped first electrode member 10, with the third electrode member of the cup-shaped form constituting the closed ionization chamber. Also, a protective cap 16 is provided for the sake of protection since the first electrode member 10 is held at a potential of several volts. This cap 16 is formed with windows 16a substantially overlapping corresponding openings 10c in the first electrode member 10, and an insect-proof net 17 is provided at each of the windows 16a. These windows are made sufficiently large compared to the openings 10c to avoid unnecessary increase of the flow resistance.

FIG. 14b shows a still further embodiment. Here, the insulating base is provided with a central cylindrical portion 14' of the same material. A second electrode member 11 of a plate-like form is supported in an intermediate part of the cylindrical portion 14', and a transversal metal member 110 is fixed to the lower open end of the cylindrical portion. The transversal member 110 divides the interior of the cup-shaped first electrode member 10 into upper and lower sections 10a and 10b, and opening means 11a for communication between these sections is provided. A fourth electrode member 15 is disposed within part of the interior of the cylindrical portion 14' on the side of the second electrode member 11 opposite the transversal member 110. The fourth electrode member 15 and transversal member 110 are provided with respective radioactive ray sources RI.

Air streams entering through some of the openings 10c into the upper section 10a within the first electrode member 10 chiefly flow round in the space between second electrode member 11 and transversal member 110, while forming dew under this flow regulated circumstance and giving heat to the transversal member 110, thus rendering the temperature condition of the relevant radioactive ray source RI to be in the proximity of that of the air streams. As an example of the relation of the first, second and fourth electrode members 10, 11 and 15 to one another, the first electrode member 10 is used as an outer electrode; the second electrode member 11 as an intermediate electrode and the fourth electrode member 15 as an inner electrode, thus forming two pairs of opposing electrodes. Designated at E are terminals connected to inner and outer electrodes 15 and 10 respectively. Other combinations of electrodes than the above example are also possible to form desired opposing electrode pairs. In this embodiment, the bottom wall of the lower section 10b is formed with radially spaced test holes or openings 10d by forming respectively corresponding raised or bent portions 10e, and also the protective cap 16 is formed with corresponding test holes 16d. (This arrangement is also shown in FIG. 9a.) These test holes find their role when periodically checking the performance of the installed smoke sensor, and intrusion of air streams through these test holes can almost be ignored; even if air enters through these holes, it is small in quantity, so that formation of dew liable to affect the stability of performance of the lower section 10b will be avoided inasmuch as air already occupying this section is reduced in relative humidity and the main metal parts are held under an adequate temperature condition.

FIG. 14c shows a yet further embodiment, which uses two planar second electrode members 11 and 11'. Here, one second electrode member 11', the transversal member 110 and the other second electrode member 11 are mounted in the mentioned order in insulating cylindrical portion 14' depending from insulating base 12. These members are electrically insulated from one another by the cylindrical portion 14'. A radioactive ray source RI is carried by fourth electrode member 15 opposing and constituting an electrode pair with the first-mentioned second electrode member 11', while another radioactive ray source RI is carried by transversal member 110 dividing the interior of first electrode member 10 into upper and lower sections 10a and 10b. With this arrangement, dew that can be formed from moisture brought in by the entering air stream will be preferentially formed on the transversal member 110, so that the possibility of dew attachment to the second electrode member 11 extending below the transversal member can be reduced. The transversal member 110 is provided with opening means of various types for permitting the air stream to the lower section 10b; in the instant embodiment, holes are formed to this end.

As has been shown in connection with the preceding embodiments, the second electrode member or transversal member constituting the upper section defined within the cup-shaped first electrode member, to which upper section external air streams are directly permitted, enables dew to be preferentially formed on the wall surfaces forming the upper section owing to its thermal conductivity. For example, aluminum which is a good thermal conductor (with a thermal conductivity of 2.38 joul/cm.sec..k. (k being the temperature difference) enables formation of much dew compared to stainless steel which is a slightly inferior thermal conductor (with a thermal conductivity of 0.151 joul/cm.sec..k). On the other hand, if synthetic resins which are thought to be non-conductor of heat, for instance polyethylene with a conductivity of 2.5 to 3.3 × 10$^{-3}$ joul/cm.sec..k, are used for transversal member, dew is not attached to the surface of this member but to the surfaces of other component parts made of metal. It is the surface of the radioactive ray source that presents the trouble of a great change of impedance due to the attachment of dew, and to avoid the attachment of dew to that surface ordinary metals which are usually though to be good thermal conductors may be used. In other words, the material which is capable of taking heat from the air stream and transmit it to the vicinity of the radioactive ray source can also permit preferential dew formation on its surface, while effectively rendering small the temperature difference between the temperature of the air stream and that of the radioactive ray source to maintain the two temperatures so close to each other that the condition necessary for the formation of dew will be satisified.

This effect can be proved even under considerably relentless situations as will be shown below. The table below demonstrates that formation of dew on the surface in the neighborhood of the radioactive ray source can be suppressed even when air streams of the listed type are caused to enter two smoke sensors, one using aluminum for the second electrode member or transversal member and the other using stainless steel for that member.

| Material | Aluminum | Stainless steel |
| --- | --- | --- |
| Temperature of the sensor | 0° C. | 20° C. |
| Conditions of air stream | Temperature: 40° C. Rel. humidity: 95% | Temperature: 40° C. Rel. humidity: 95% |
| Wall surfaces forming the upper chamber | Much dew is formed. | Considerable dew is formed. |
| Neighborhood of the radioactive ray source | No dew is formed. | No dew is formed. |
| Wall surfaces forming the lower section | No dew is formed. | Slight dew is formed. |

While the preferential formation of dew can be effectively attained in the upper section formed within the first electrode member, the dew that is formed can be spontaneously evaporated, so that no particular evaporating heater is needed in case of the usual residence or space for use. The smoke sensor according to the invention is particularly worthwhile for use in a place near switch kitchens and bath rooms where very humid air streams are readily produced, and when used in such places it will reliably monitor the fire level present depending upon the type of fire used and ensure reliable fire prevention without the possiblity of malfunction as is often encountered with the prior-art smoke sensors.

What is claimed is:

1. A smoke sensor of the ionization type comprising a first metal electrode member having a cup-shaped configuration and provided with air inlet means for permitting an air current to flow into the inner space of said first electrode member, a second metal electrode arranged within said first cup-shaped, electrode member and defining within the latter an upper section and a lower section thereof, said air current flowing into said upper section through said air inlet means and circulating in said upper section before flowing into said lower section, a flow regulating means provided within said upper section and serving at least to change the direction of the air current in said upper section, a radioactive ray source carried by said second electrode member so as to radiate in said lower section, said second electrode member having opening means therethrough to permit the inflowing air current to flow from said upper section into said lower section, whereby the formation of dew is preferentially caused within said upper section and the heat retained by the inflowing air current is transferred to said second electrode member carrying said radioactive ray source such that the temperature of the second electrode member approaches that of said inflowing air current.

2. A smoke sensor according to claim 1, wherein said upper and lower sections are defined by a transverse member made of a good thermal conductor and disposed within said first electrode member, said radioactive ray source being carried by said transversal member, said second electrode member being supported by said transversal member via an insulating means, said opening means communicating with upper and lower sections being formed in said transversal member.

3. A smoke sensor according to claim 1, which further comprises a third electrode member constituting a closed ionization chamber and disposed in said upper section, said second electrode member extending transversely within said first electrode member and being joined to said third electrode member.

4. A smoke sensor according to claim 1, wherein said second electrode member is provided with an annular peripheral projection serving to cause whirling of the air current.

5. A smoke sensor according to claim 1, wherein said second electrode member is provided with fins adjacent to said opening means.

6. A smoke sensor according to claim 2, wherein said transversal member is provided with an annular peripheral projection.

7. A smoke sensor according to claim 2, wherein said transversal member is provided with fin means.

* * * * *